(12) United States Patent
Kacelenga (10) Patent No.: US 10,860,103 B2
(45) Date of Patent: Dec. 8, 2020

(54) ENHANCING VIRTUAL REALITY WITH PHYSIOLOGICAL SENSING

(71) Applicant: Dell Products, L.P., Round Rock, TX (US)

(72) Inventor: Ray Vivian Kacelenga, Cedar Park, TX (US)

(73) Assignee: Dell Products, L.P., Round Rock, TX (US)

( * ) Notice: Subject to any disclaimer, the term of this patent is extended or adjusted under 35 U.S.C. 154(b) by 0 days.

(21) Appl. No.: 16/135,932

(22) Filed: Sep. 19, 2018

(65) Prior Publication Data
US 2020/0089321 A1     Mar. 19, 2020

(51) Int. Cl.
*G06F 3/01* (2006.01)
*G06T 19/00* (2011.01)
(Continued)

(52) U.S. Cl.
CPC .......... *G06F 3/015* (2013.01); *A61B 5/02055* (2013.01); *A61B 5/165* (2013.01); *A61B 5/6803* (2013.01); *G06F 3/016* (2013.01); *G06T 19/006* (2013.01); *A61B 5/02438* (2013.01); *A61B 5/0488* (2013.01); *A61B 5/0533* (2013.01); *A61B 2503/12* (2013.01); *G02B 27/0172* (2013.01); *G02B 2027/014* (2013.01); *G06F 2203/011* (2013.01)

(58) Field of Classification Search
CPC .... G06F 3/015; G06F 3/016; G06F 2203/011; A61B 5/02055; A61B 5/165; A61B 5/6803; A61B 5/02438; A61B 5/0488; A61B 5/0533; A61B 2503/12; G06T 19/006; G02B 27/0172; G02B 2027/014; G02B 2203/011
See application file for complete search history.

(56) References Cited

U.S. PATENT DOCUMENTS

| 10,258,288 B2 * | 4/2019 | Penders | A61B 5/7221 |
| 2010/0217099 A1 * | 8/2010 | LeBoeuf | A61B 5/00 600/301 |

(Continued)

OTHER PUBLICATIONS

Kacelenga et al., "Voting Fusion Adaptation for Landmine Detection," 2002, pp. 333-340.

*Primary Examiner* — Patrick N Edouard
*Assistant Examiner* — Eboni N Giles
(74) *Attorney, Agent, or Firm* — Fogarty LLP (57) ABSTRACT

A virtual, augmented, or mixed reality (xR) session is hosted in a physical environment. Physiological measurements of an individual wearing a Head-Mounted Device (HMD) are captured while the individual participates in the xR session. An environmental context of the xR session is determined based on measurements of environmental properties of the physical environment. Physiological states of the individual are determined based on the physiological data. Multiple physiological states may be determined by independent chains that evaluate independent physiological data streams. The environmental context and the physiological states are combined, according to data fusion techniques such as algebraic voting, to determine a physiological classification of the individual. The xR session is modified based on the physiological user classification.

20 Claims, 6 Drawing Sheets

(51) Int. Cl.
    *A61B 5/0205*     (2006.01)
    *A61B 5/16*     (2006.01)
    *A61B 5/00*     (2006.01)
    G02B 27/01     (2006.01)
    A61B 5/024     (2006.01)
    A61B 5/0488     (2006.01)

(56) References Cited

U.S. PATENT DOCUMENTS

| | | | |
|---|---|---|---|
| 2018/0190376 A1* | 7/2018 | Hill | A61B 5/0482 |
| 2019/0046044 A1* | 2/2019 | Tzvieli | A61B 5/015 |
| 2019/0110755 A1* | 4/2019 | Capodilupo | G06K 9/6282 |
| 2019/0269914 A1* | 9/2019 | Moaddeb | A61B 5/02241 |
| 2019/0313915 A1* | 10/2019 | Tzvieli | A61B 5/015 |

* cited by examiner

ENHANCING VIRTUAL REALITY WITH PHYSIOLOGICAL SENSING

FIELD

The present disclosure generally relates to virtual, augmented, and mixed reality (xR) applications, and, more particularly, to the use of physiological data in xR applications hosted by Information Handling Systems (IHSs).

BACKGROUND

As the value and use of information continues to increase, individuals and businesses seek additional ways to process and store information. One option available to users is Information Handling Systems (IHSs). An IHS generally processes, compiles, stores, and/or communicates information or data for business, personal, or other purposes thereby allowing users to take advantage of the value of the information. Because technology and information handling needs and requirements vary between different users or applications, IHSs may also vary regarding what information is handled, how the information is handled, how much information is processed, stored, or communicated, and how quickly and efficiently the information may be processed, stored, or communicated. The variations in IHSs allow for IHSs to be general or configured for a specific user or specific use such as financial transaction processing, airline reservations, enterprise data storage, or global communications. In addition, IHSs may include a variety of hardware and software components that may be configured to process, store, and communicate information and may include one or more computer systems, data storage systems, and networking systems.

In modern applications, IHSs may be used to produce virtual, augmented, or mixed reality (xR) applications. The goal of virtual reality (VR) is to immerse users in virtual environments. A conventional VR system includes an HMD (Head Mounted Display) that may be worn by a user in similar manner to a pair of goggles and obscure the wearer's real-world surroundings, such that only digitally-generated images are visible via displays elements incorporated into the HMD.

In contrast, augmented reality (AR) and mixed reality (MR) operate by overlaying digitally-generated content or entities (e.g., characters, text, hyperlinks, images, graphics, etc.) upon the user's real-world, physical surroundings. A typical AR/MR device includes a projection-based optical system that displays content on a translucent or transparent surface of an HMD, heads-up display (HUD), eyeglasses, or the like (collectively "HMDs").

In some implementations, an HMD may be coupled to a host IHS that supports the xR applications provided via the HMD. In most scenarios, an HMD has more limited processing capabilities than the host IHS, so the host IHS may be used to generate some or all of the digital images that are displayed by the HMD. The HMD transmits information to the host IHS regarding the state of the user, which in turn enables the host IHS to determine which image or frame to show to the user next, and from which perspective, as the user moves in within the physical environment in which the xR session is conducted.

HMDs may incorporate various motion sensors for tracking the user's head orientation. HMDs also typically include cameras for tracking the user's gaze and identifying features in the physical environment. In addition, an HMD may capture verbal commands and other audio inputs by the user. This captured audio and eye-tracking information are used to synchronize the video frames and audio content of the xR session with the user's head orientation and position as determined by the motion sensors. Typical HMDs do not monitor or utilize additional types of user state information.

SUMMARY

In various embodiments, a method provides for hosting a virtual, augmented, or mixed reality (xR) session in a first physical environment, where the method includes: receiving a plurality of physiological data streams, each of the data streams comprising physiological measurements of an individual wearing a Head-Mounted Device (HMD) while participating in the xR session; receiving a plurality of environmental state data streams comprising measurements of environmental properties of the first physical environment; determining a plurality of physiological states of the individual based on each of the respective plurality of physiological data streams; combining the plurality of physiological states based on the environmental state data to determine a physiological user classification; and modifying the xR session based on the physiological user classification.

In some embodiments of the method, a first portion of the physiological data streams are generated by physiological sensor components of the HMD. In some embodiments of the method, the plurality of physiological states are combined further based on an activity of the user while participating in the xR session. In some embodiments of the method, the physiological user classification indicates a physiological stress level of the individual while participating in the xR session. In some embodiments of the method, the xR session is modified by changing an intensity level of the xR session in response to the physiological stress level of the individual. In some embodiments of the method, a first physiological data stream of the plurality of data streams is processed by a first processing chain to determine a first physiological user state and a second physiological data stream of the plurality of data streams is processed by a second processing chain to determine a second physiological user state. In some embodiments of the method, the first physiological user state and the second physiological user state are combined based on algebraic voting logic based on respective confidence levels of the first and second user states.

In various additional embodiments, a Head-Mounted Device (HMD) configured for participating in a virtual, augmented, or mixed reality (xR) session in a first physical environment, includes: a processor; a plurality of physiological sensors, each physiological sensor generating a data stream including physiological measurements of an individual wearing the HMD while participating in the xR session; and a memory coupled to the processor, the memory having program instructions stored thereon that, upon execution, cause the first HMD to: transmit the plurality of physiological data streams to a host IHS (Information Handling System), wherein a plurality of physiological states of the individual are determined by the host IHS based on each of the respective plurality of physiological data streams; collecting environmental state data comprising measurements of environmental properties of the first physical environment; transmitting the environmental state data to the host IHS, wherein the plurality of physiological states are combined by the host IHS based on the environmental state data to determine a physiological user classification, and wherein the xR session is modified based on the physiological user classification; and presenting the modified xR session to the individual.

In some embodiments of the HMD, the environmental data is collected by querying an xR component located in the first physical environment. In some embodiments of the HMD, the physiological user classification indicates a physiological stress level of the individual while participating in the xR session. In some embodiments, the HMD further includes a plurality of haptic feedback components activated in response to the physiological user classification. In some embodiments of the HMD, the plurality of haptic feedback components comprises a warmer that is activated if the physiological stress level of the individual is below a first threshold. In some embodiments of the HMD, the wherein the xR session is modified by changing an intensity level of the xR session in response to the physiological stress level of the individual. In some embodiments of the HMD, the plurality of physiological sensors comprises at least one of an electromyography sensor, gravimetric skin response sensor, a heart rate sensor and a body temperature sensor.

In various additional embodiments, a system hosts a virtual, augmented, or mixed reality (xR) session in a first physical environment. The system includes: a Head-Mounted Device (HMD) comprising a plurality of physiological sensors, each physiological sensor generating a data stream including physiological measurements of an individual wearing the HMD while participating in the xR session; and a host IHS (Information Handling System) coupled to the HMD and configured to: receive the plurality of physiological data streams; receive a plurality of environmental state data streams comprising measurements of environmental properties of the first physical environment; determine a plurality of physiological states of the individual based on each of the respective plurality of physiological data streams; combine the plurality of physiological states based on the environmental state data to determine a physiological user classification; and modify the presentation of the xR session to the individual by the HMD based on the physiological user classification.

In some embodiments of the system, the plurality of physiological states are combined further based on an activity of the user while participating in the xR session. In some embodiments of the system, the physiological user classification indicates a physiological stress level of the individual while participating in the xR session. In some embodiments of the system, the xR session is modified by changing an intensity level of the xR session in response to the physiological stress level of the individual. In some embodiments of the system, a first physiological data stream of the plurality of data streams is processed by a first processing chain to determine a first physiological user state and a second physiological data stream of the plurality of data streams is processed by a second processing chain to determine a second physiological user state. In some embodiments of the system, the first physiological user state and the second physiological user state are combined based on voting based on respective confidence levels of the first and second user states.

BRIEF DESCRIPTION OF THE DRAWINGS

The present invention(s) is/are illustrated by way of example and is/are not limited by the accompanying figures. Elements in the figures are illustrated for simplicity and clarity, and have not necessarily been drawn to scale.

DETAILED DESCRIPTION

Embodiments described herein provide systems and methods for collaborating between Head-Mounted Devices (HMDs) in virtual, augmented, and mixed reality ("xR") applications in order to more quickly and efficiently join additional HMDs to an ongoing co-located xR session. These techniques are particularly useful in xR applications that employ HMDs, Heads-Up Displays (HUDs), and eyeglasses-collectively referred to as "HMDs."

Figure 1:
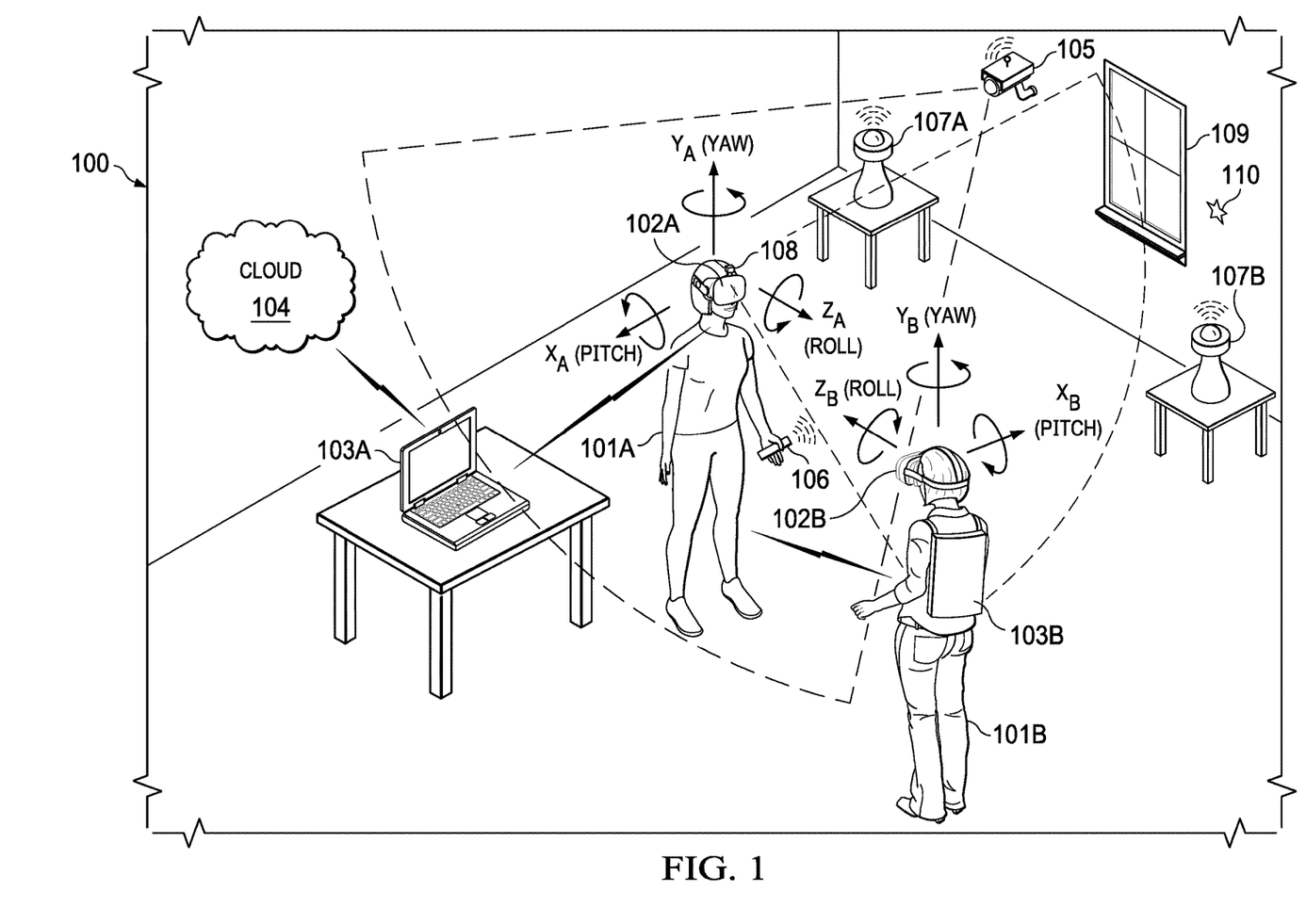
FIG. 1 is a perspective view of an example of an environment including Head-Mounted Displays (HMDs) participating in an xR session, according to some embodiments.

FIG. 1 is a perspective view of an example of physical environment 100 having co-located HMDs 102A and 102B. As illustrated, user 101A wears HMD 102A around their head and over their eyes during execution of an xR application. Similarly, user 101B wears HMD 102B. In this non-limiting example, HMD 102A is tethered to host Information Handling System (IHS) 103A via a wireless connection, and HMD 102B is tethered by a wired connection to host IHS 103B that is worn by user 101B.

In co-located environment 100 hosting an xR session, multiple components may interoperate in running xR applications for use by user 101A and 101B. For instance, an xR application session being conducted in environment 100 may include a subset of components or objects operated by HMD 102A and another subset of components or objects operated by host IHS 103A; as well as a subset of components or objects operated by HMD 102B, and another subset of components or objects operated by host IHS 103B.

Particularly, host IHS 103A may be used to generate digital images to be displayed by HMD 102A. In turn, HMD 102A may transmit information to host IHS 103A regarding the state of user 101A, such as physical position, pose or head orientation, gaze focus, etc., which enables host IHS 103A to determine which image or frame to display to the user next, and from which perspective. In a corresponding manner, IHS 103B may generate digital images to be displayed by HMD 102B based on the state of user 101B. In this example, host IHS 103B is built into (or otherwise coupled to) a backpack or vest, wearable by user 101B and host IHS 103A.

As user 101A moves about environment 100, changes in: (i) physical location (e.g., Euclidian or Cartesian coordinates x, y, and z) or translation; and/or (ii) orientation (e.g., pitch, yaw, and roll) or rotation, cause host IHS 103A to effect a corresponding change in the picture or symbols displayed to user 101A via HMD 102A, usually in the form of one or more rendered video frames. Similarly, as user 101B moves, changes in HMD 102B's physical location or translation; and/or HMD 102B's orientation or rotation, cause host IHS 103B to effect corresponding changes in the video frames displayed to user 101B via HMD 102B.

Movement of the user's head and gaze may be detected by HMD 102A and processed by host IHS 103A, for example, to render video frames that maintain visual congruence with the outside world and/or to allow user 101A to look around a consistent xR session. In some cases, xR application components executed by HMDs 102A-B and IHSs 103A-B may provide a cooperative, at least partially shared, xR session between users 101A and 101B, such as in the form of a video game, 3-D modeling and/or a productivity (e.g., a virtual meeting) application.

As used herein, the term "Simultaneous Localization and Mapping" or "SLAM" refers systems and methods that use positional tracking devices to construct a map of an unknown physical environment in which an HMD is located, and that simultaneously identifies where an HMD is located within the physical environment. SLAM methods may also identify other positional information regarding an HMD, such as an HMD's orientation and/or pose within the physical environment.

Generally, SLAM methods implemented in connection with xR applications may include a propagation component, a feature extraction component, a mapping component, and an update component. The propagation component may receive angular velocity and accelerometer data from an Inertial Measurement Unit (IMU) built into the HMD, for example, and it may use that data to produce a new HMD position and/or pose estimation, which may be used to propagate a new state of an xR session. A camera (e.g., a depth-sensing camera) may provide video frames to the feature extraction component, which extracts useful image features (e.g., using thresholding, blob extraction, template matching, etc.), and generates a descriptor for each feature. These features, also referred to as "landmarks," are then fed to the mapping component.

To enable positional tracking for SLAM purposes, HMDs 102A-B may use wireless, inertial, acoustic, or optical sensors. And, in many embodiments, different SLAM methods may use different positional tracking sources and/or devices. For example, wireless tracking may use a set of anchors or lighthouses 107A-B that are placed at locations within environment 100. Wireless tracking may also use one or more tokens 106 that may be held or attached to a user during an xR session. In addition, wireless tracking may also use one or tags 110 that may be positioned at various locations within environment 100 and may serve as reference points. Using such sources of wireless tracking information, HMDs 102A-B may triangulate their respective positions and/or states. Inertial tracking may use data from accelerometers and gyroscopes within HMDs 102A-B to find a velocity and position of HMDs 102A-B relative to some initial point. Acoustic tracking may use sonic sensors to determine the position of HMDs 102A-B.

Optical tracking may include any suitable computer vision algorithm and tracking device, such as a camera of visible, infrared (IR), or near-IR (NIR) range, a stereo camera, and/or a depth camera. With inside-out tracking using markers, for example, camera 108 may be embedded in HMD 102A, and infrared markers 107A-B or tag 110 may be placed in known stationary locations. With outside-in tracking, camera 105 may be placed in a stationary location and infrared markers 106 may be placed on HMDs 102A or held by user 101A. In other cases, markerless inside-out tracking may use continuous searches and feature extraction techniques from video frames obtained by camera 108 (e.g., using visual odometry) to find natural visual landmarks (e.g., window 109) in environment 100.

In various embodiments, data obtained from a positional tracking system and technique employed by HMDs 102A-B may be received by host IHSs 103A-B, which in turn execute one or more SLAM methods utilized by an xR application. In the case of an inside-out SLAM method, for example, an xR application receives the position and orientation information from HMDs 102A-B, determines the position of features extracted from the images captured by camera 108, and corrects the localization of landmarks in space using comparisons and predictions.

As described in additional detail with regard to the below embodiments, an xR application may monitor parameters describing the environment 100 in which the xR session is being conducted. For instance, in certain embodiments, anchors or lighthouses 107A-B may include sensors that measure environmental parameters such as ambient temperature, relative humidity, atmospheric pressure, and ambient light within environment 100. The host IHSs 103A-B and the HMDs 102A-B may query the anchors or lighthouses 107A-B in order to obtain current environmental conditions. This data provides an environmental context for evaluating physiological sensor readings obtained by HMDs 102A-B that monitor various physiological characteristics of the respective users 101A-B. In certain embodiments, such environmental monitoring may be performed by sensors integrated in various other components participating in the xR session, such as stationary camera 105, landmark 110 and IHSs 103A-B.

Figure 2:
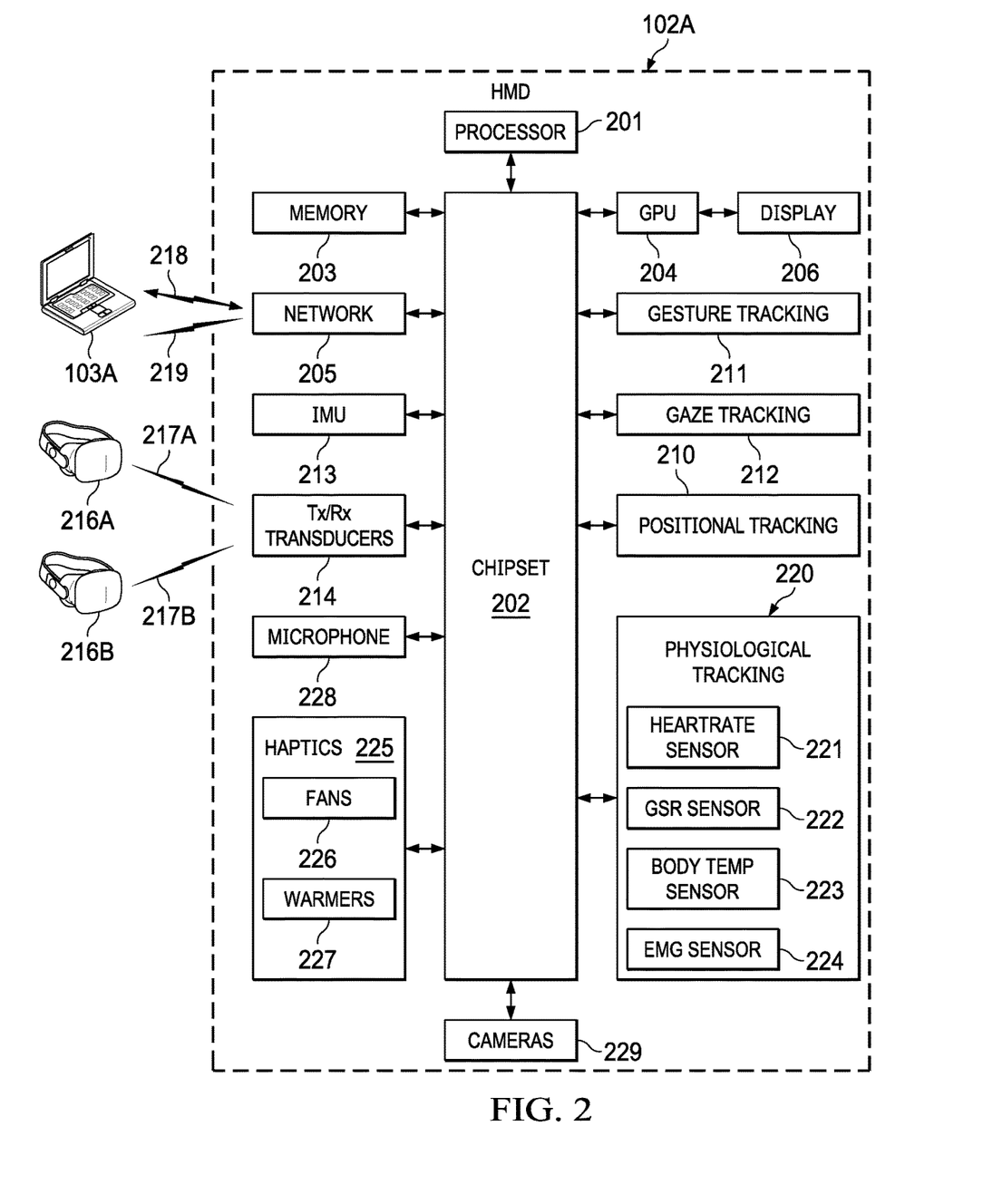
FIG. 2 is a diagram of an example of an HMD configured for collection of physiological sensor data, according to some embodiments.

FIG. 2 is a block diagram illustrating certain components of an example HMD 102A that may be utilized within an xR system, according to some embodiments, for collecting and utilizing physiological state information pertaining to the individual wearing HMD 102A. As depicted, HMD 102A includes components configured to create and/or display an all-immersive virtual environment; and/or to overlay digitally-created content or images on a display, panel, or surface (e.g., an LCD panel, an OLED film, a projection surface, etc.) in place of and/or in addition to the user's natural perception of the real-world.

As shown, HMD 102A includes processor 201. In various embodiments, HMD 102A may be a single-processor system, or a multi-processor system including two or more processors. Processor 201 may include any processor capable of executing program instructions, such as a PENTIUM series processor, or any general-purpose or embedded processors implementing any of a variety of Instruction Set Architectures (ISAs), such as an x86 ISA or a Reduced Instruction Set Computer (RISC) ISA (e.g., POWERPC, ARM, SPARC, MIPS, etc.). HMD 102A includes chipset 202 coupled to processor 201. In various embodiments, chipset 202 provides processor 201 with access to a number of resources.

For instance, chipset 202 provides processor 201 and/or graphics processor unit (GPU) 204 with access to memory 203. In various embodiments, memory 203 may be implemented using any suitable memory technology, such as static RAM (SRAM), dynamic RAM (DRAM), or any nonvolatile/Flash-type memory, such as a solid-state drive (SSD) or the like. Memory 203 may store program instructions that, upon execution by processor 201 and/or GPU 204, present an xR application to user 101A wearing HMD 102A, and may also present all or a portion of the xR application to provider to another participant in an xR session.

Chipset 202 may also be coupled to network interface 205 to support communications via various wired and/or wireless networks. For instance, as described regard to FIG. 1, an HMD may be coupled to a host IHS via a wired connection 218 that may be supported by network interface 205, such as the tether connecting HMD 102B to IHS 103B that is worn by the user 101B. Network interface 205 may also support a wireless connection 219 between HMD 102A and a host IHS, such as the wireless connection with IHS 103A.

Chipset 202 may also be coupled to display controller or graphics processor (GPU) 204 via a graphics bus, such as an Accelerated Graphics Port (AGP) or Peripheral Component Interconnect Express (PCIe) bus. As shown, graphics processor 204 provides video or display signals to display 206. As described, the display 206 of HMD 102A may include an immersive display element within a head-mounted device that is worn by a user participating in an xR session. In certain embodiments display 206 may consist of separately-controlled left and right display elements. In certain instances, the information provided via display 206 may be generated in full or in part by a host IHS 103A by which HMD 102A participates in the xR session.

Other resources that may be coupled to processor 201 of HMD 102A through chipset 202 may include, but are not limited to, positional tracking system 210, gesture tracking system 211, gaze tracking system 212, inertial measurement unit (IMU) system 213, and physiological tracking system 220.

Positional tracking system 210 may utilize one or more cameras 229 or other optical sensors (e.g., a camera 108) configured to determine the movements of HMD 102A in relation to environment 100. For example, an inside-out tracking system 210 may be configured to implement markerless tracking techniques that use distinctive visual characteristics of the physical environment to identify specific images or shapes which are then usable to calculate HMD 102A's position and orientation within the environment 100.

Gesture tracking system 211 may utilize one or more cameras 229 or other optical sensors that enable user 101 to use their hands for virtual interaction with objects rendered by the visual display 206 of HMD 102A. For example, gesture tracking system 211 may be configured to implement hand tracking and gesture recognition in a 3D-space via a user-facing 2D camera 229 or other optical sensor. In some cases, gesture tracking system 211 may track a selectable number of degrees-of-freedom (DOF) of motion, with depth information, to recognize dynamic gestures (e.g., swipes, clicking, tapping, grab and release, etc.) usable to control or otherwise interact with xR applications executed by HMD 102A and/or a host IHS to which HMD 102A may be coupled.

Gaze tracking system 212 may include an inward-facing projector configured to create a pattern of infrared (or near-infrared) light on the user's eyes, and an inward-facing camera 229 configured to take high-frame-rate images of the eyes and their reflection patterns, which are then used to calculate the user's eye's position and gaze point. In some cases, gaze detection or tracking system 212 may be configured to identify a direction, extent, and/or speed of movement of the user's eyes in real-time, during execution of an xR application.

IMU system 213 may include one or more accelerometers and gyroscopes configured to measure and report a specific force and/or angular rate of movement of the user's head. In some cases, IMU system 213 may be configured to a detect a direction, extent, and/or speed of rotation (e.g., an angular speed) of the user's head in real-time, during execution of an xR application.

HMD 102A may utilize a physiological tracking system 220 that includes a variety of sensors that support monitoring of physiological characteristics of the user wearing the HMD. As described in additional detail with regard to the below embodiments, the physiological parameters measured by the sensors may be collected and utilized in evaluating and categorizing the physiological state of the user. This physiological state information may then be used to modify various aspects of the xR session in response to the physiological state of the user.

As illustrated, the physiological tracking system 220 HMD 102A may include a heartrate sensor 221 that monitors the user heart beat and, in some cases, heartrate variability, thus providing an indication of the user's stress, excitement, and/or mood. HMD 102A may also include a gravimetric skin response (GSR) sensor 222 utilized to monitor the user's sweat level, thus providing an indication of stress, fright and/or thermal stress by the user. The physiological tracking system 220 of HMD 102A may also include an electromyography (EMG) sensor 224 for measuring the user's muscle activity, which may be used for inferring degrees of emotional tension or levels of physical activity by the user. The physiological tracking system 220 may also utilize a body temperature sensor 223 that measures the user's temperature. In certain embodiments, one or more of the sensors of the physiological tracking system 220 may be additionally or alternatively incorporated in a device worn or held by the user, such as markers 106 of FIG. 1.

As illustrated, HMD 102A may include one or more digital microphones 228 that may be used to capture verbal commands from the user, as well as capturing other audio inputs from the user and, in some scenarios, ambient environmental audio information. As described with regard to the below embodiments, the audio captured via microphones 228 may be utilized, as with the sensors of the physiological system 220, in the evaluation of the physiological state of the user, which may then be utilized to adjust various aspects of the xR session.

In certain embodiments, HMD 102A may also include a haptics system 225 for providing the user with sensory feedback as part of an xR session. For instance, the haptics system 225 of HMD 102A may include microfans 226 that may be used to cool the user or to augment the user's xR experience with additional sensory information. The haptics system 225 may likewise include warmers 227 that may be similarly used to augment the xR experience of the user with sensory information in the form of heat. As described below, in certain embodiments, the sensory information provided via haptics system 225 may be selected and configured based on the user's physiological state, as determined by the sensor data captured by the physiological tracking system 220 and transmitted to the host IHS 103A.

In some implementations, HMD 102A may communicate with a host IHS 103A via a wired connection 218, such as a cable by which IHS 103A may be tethered to and worn by a user, such as IHS 103B of FIG. 1. HMD 102A may also communication with a host IHS 103A via wireless connections 219 (e.g., WiGig, WiFi, etc.). For example, if host IHS 103A has more processing power and/or better battery life than HMD 102A, host IHS 103A may be used to offload some of the processing involved in the creation of the xR experience. In certain embodiments, the physiological sensor data, including audio, that is captured by HMD 102A may be streamed via the tether to the host IHS 103A, where this physiological state data may be used to evaluate and classify the user's physiological state.

In various embodiments, HMD 102A may not include each of the components shown in FIG. 2. Additionally, or alternatively, HMD 102A may include components in addition to those shown in FIG. 2. Furthermore, components represented as discrete entities in FIG. 2 may, in some embodiments, be integrated with other components. In various implementations, all or a portion of the functionality provided by the illustrated components may be provided by components integrated as a System-On-Chip (SOC), or the like.

Figure 3:
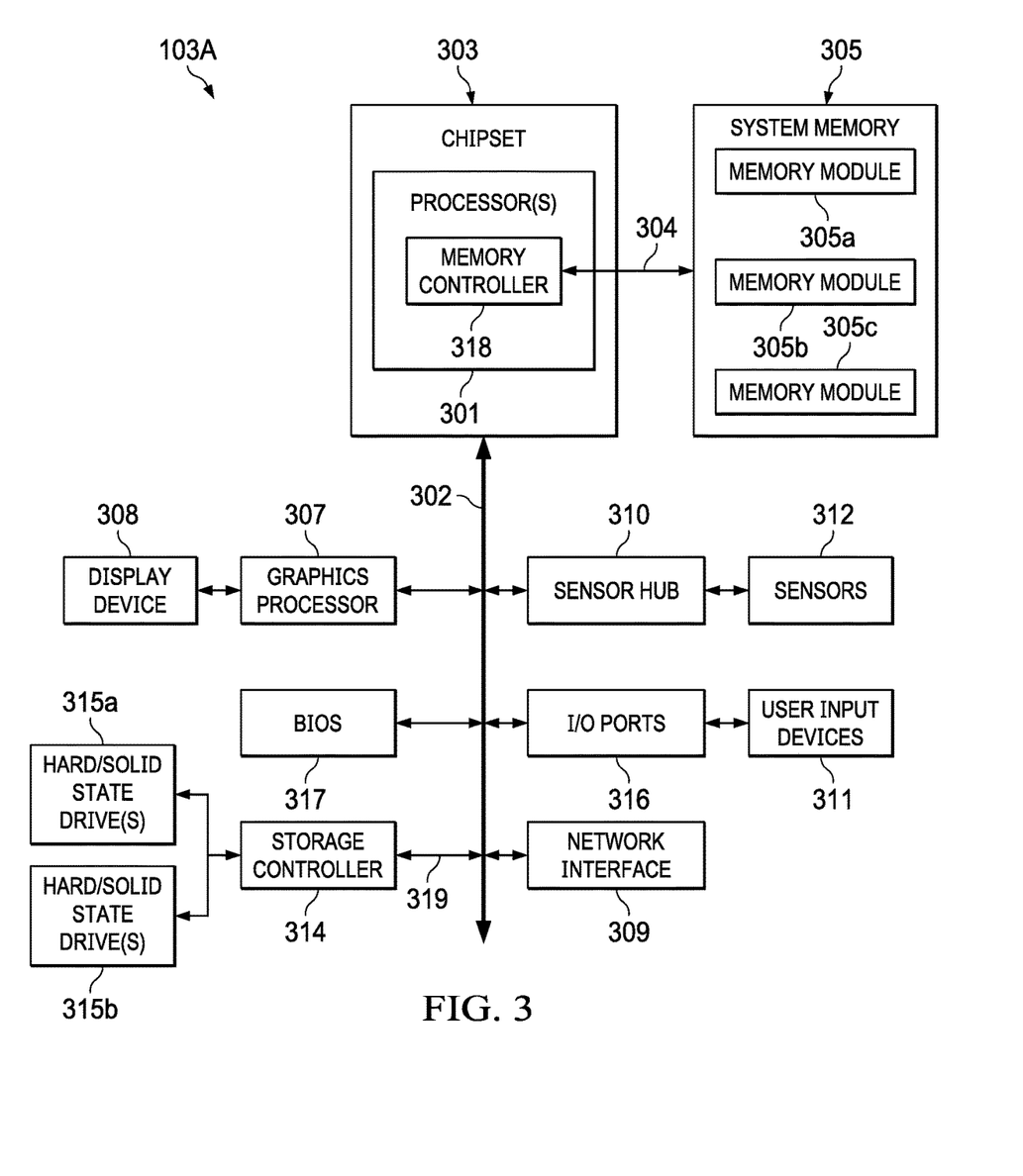
FIG. 3 is a diagram of a host Information Handling System (IHS) configured for analysis and use of physiological and environmental sensor data within a hosted xR session, according to some embodiments.

FIG. 3 is a block diagram illustrating certain components of an example IHS 103A, according to some embodiments, that may be utilized within an xR system for utilizing physiological state information and environmental context information in order to modify various aspects of the xR session in response to physiological state of the user. For purposes of this disclosure, an IHS may include any instrumentality or aggregate of instrumentalities operable to compute, calculate, determine, classify, process, transmit, receive, retrieve, originate, switch, store, display, communicate, manifest, detect, record, reproduce, handle, or utilize any form of information, intelligence, or data for business, scientific, control, or other purposes. For example, an IHS may be a personal computer (e.g., desktop or laptop), tablet computer, mobile device (e.g., Personal Digital Assistant (PDA) or smart phone), server (e.g., blade server or rack server), a network storage device, or any other suitable device and may vary in size, shape, performance, functionality, and price. An IHS may include Random Access Memory (RAM), one or more processing resources such as a Central Processing Unit (CPU) or hardware or software control logic, Read-Only Memory (ROM), and/or other types of nonvolatile memory. Additional components of an IHS may include one or more disk drives, one or more network ports for communicating with external devices as well as various I/O devices, such as a keyboard, a mouse, touchscreen, and/or a video display. An IHS may also include one or more buses operable to transmit communications between the various hardware components.

IHS 103A includes one or more processors 301, such as a Central Processing Unit (CPU), to execute code retrieved from a system memory 305. Although IHS 103A is illustrated with a single processor 301, other embodiments may include two or more processors, that may each be configured identically, or to provide specialized processing functions. Processor 301 may include any processor capable of executing program instructions, such as an Intel Pentium™ series processor or any general-purpose or embedded processors implementing any of a variety of Instruction Set Architectures (ISAs), such as the x86, POWERPC®, ARM®, SPARC®, or MIPS® ISAs, or any other suitable ISA.

In FIG. 3, the processor 301 includes an integrated memory controller 318 that may be implemented directly within the circuitry of the processor 301, or the memory controller 318 may be a separate integrated circuit that is located on the same die as the processor 301. The memory controller 318 may be configured to manage the transfer of data to and from the system memory 305 of the IHS 103A via a high-speed memory interface 304.

The system memory 305 that is coupled to processor 301 via the memory bus 304 provides the processor 301 with a high-speed memory that may be used in the execution of computer program instructions by the processor 301. Accordingly, system memory 305 may include memory components, such as such as static RAM (SRAM), dynamic RAM (DRAM), NAND Flash memory, suitable for supporting high-speed memory operations by the processor 301. In certain embodiments, system memory 305 may combine both persistent, non-volatile memory and volatile memory.

In certain embodiments, the system memory 305 may be comprised of multiple removable memory modules. The system memory 305 of the illustrated embodiment includes three removable memory modules 305a, 305b and 305c. Each of the removable memory modules 305a-c may correspond to a motherboard memory socket that receives a removable memory module 305a-c, such as a DIMM (Dual In-line Memory Module), that can be coupled to the socket and then decoupled from the socket as needed, such as to upgrade memory capabilities or to replace faulty components. Other embodiments of IHS 103A may be configured with memory socket interfaces that correspond to different types of removable memory module form factors, such as a Dual In-line Package (DIP) memory, a Single In-line Pin Package (SIPP) memory, a Single In-line Memory Module (SIMM), and/or a Ball Grid Array (BGA) memory.

IHS 103A utilizes a chipset 303 that may include one or more integrated circuits that are connected to processor 301. In the example of FIG. 3, processor 301 is depicted as a component of chipset 303. In other embodiments, all of chipset 303, or portions of chipset 303 may be implemented directly within the integrated circuitry of the processor 301. Chipset 303 provides the processor(s) 301 with access to a variety of resources accessible via bus 302. In IHS 103A, bus 302 is illustrated as a single element. Various embodiments may utilize any number of buses to provide the illustrated pathways served by bus 302.

As illustrated, a variety of resources may be coupled to the processor(s) 301 of the IHS 103A through the chipset 303. For instance, chipset 303 may be coupled to a network interface 309, such as provided by a Network Interface Controller (NIC) that is coupled to the IHS 103A and allows the IHS to communicate via a network, such as the Internet or a LAN. Network interface device 309 may provide IHS 103A with wired and/or wireless network connections via a variety of network technologies, such as wireless cellular or mobile networks (CDMA, TDMA, LTE etc.), WIFI and BLUETOOTH. In certain embodiments, IHS 103A may utilize network interface 309 to establish connections to other IHSs that are also hosting the participation of an HMD in an xR session, (e.g., via Ethernet, WiFi, or WiFi Direct), thus allowing the host IHSs to cooperate in the operation of the xR application.

Chipset 303 may also provide access to one or more display device(s) 308 via graphics processor 307. In certain embodiments, graphics processor 307 may be comprised within one or more video or graphics cards or an embedded controller installed as components of the IHS 103A. Graphics processor 307 may generate display information and provide the generated information to one or more display device(s) 308 coupled to the IHS 103A. In certain embodiments, graphics processor 307 may be integrated within processor 301. The one or more display devices 308 coupled to IHS 103A may utilize LCD, LED, OLED, or other thin film display technologies. Each display device 308 may be capable of touch input such as via a touch controller that may be an embedded component of display device 308, graphics processor 307, or a separate component of IHS 103A accessed via bus 302.

As described, in certain instances, processing necessary for the user's participation in an xR session may be offloaded from the user's HMD to the host IHS. For instance, the host IHS may receive various inputs from the user's HMD, such as sensor inputs describing the movements of the user. The host IHS may then process these inputs from the HMD to generate the responsive visual information to be presented to the display of the user's HMD. In such scenarios, graphics processor 307 of IHS 103A may be utilized to generate display information that is transmitted to the hosted HMD for display to the user.

In certain embodiments, chipset 303 may utilize one or more I/O ports 316 and or I/O controllers to provide access to input devices 311, such as a keyboard, mouse, touchpad, touchscreen and/or other peripheral input devices. In certain embodiments, I/O ports 316 may support a tethered connection to an HMD, such as HMD 102A that is coupled to the IHS 103A. Coupled in this manner, IHS 103A may execute and host an xR application that is displayed via the coupled HMD. In certain embodiments, I/O ports 316 may also be configured to receive xR application inputs from a connected HMD. The user input devices 316, and any HMD coupled to IHS 103A in this manner, may interface with the I/O ports 316 through wired or wireless connections.

Sensors 312 accessed via sensor hub 310 may provide access to sensor data describing environmental conditions in which the xR session is being conducted. Such environmental sensor inputs may be received from sensors integrated into the IHS 103A or via querying other components participating in the xR session, such as the lighthouses 107A-B described with respect to FIG. 1. The sensor hub 310 may also receive the physiological sensor readings collected and streamed by the physiological tracking system 220 of the HMD 102A of FIG. 2. As described with regard to the below embodiments, the sensor hub 310 may process the sensor data received from the various sources in order to determine a physiological state of the user, which may then be used in adapting the xR session, thus modifying the user's xR experience to account for their physiological state.

As illustrated, IHS 103A also includes a BIOS (Basic Input/Output System) 317 that may be stored in a non-volatile memory accessible by chipset 303 via bus 302. The BIOS 317 provides an abstraction layer that allows the operating system to interface with the hardware components of the IHS 103A. Upon powering or restarting IHS 103A, processor(s) 301 may utilize BIOS 317 instructions to initialize and test hardware components coupled to the IHS 103A, including both components permanently installed as components of the motherboard of IHS 103A and removable components installed within the various expansion slots supported by the IHS 103A. The BIOS 317 instructions may also load an operating system for use by the IHS 103A. The Unified Extensible Firmware Interface (UEFI) was designed as a successor to BIOS. As a result, many modern IHSs utilize UEFI in addition to or instead of a BIOS. As used herein, BIOS is intended to also encompass UEFI. In certain embodiments, the BIOS may be replaced, in full or in part, by a baseboard management controller (BMC) or another in-band or out-of-band controller that supports remote administration of IHS 103A.

In the illustrated embodiment, IHS 103A includes two storage drives 315a-b. In various embodiments, the storage drives 315a-b may include SAS (Serial Attached SCSI) magnetic disk drives, SATA (Serial Advanced Technology Attachment) magnetic disk drives, solid-state drives (SSDs) and other types of storage drives in various combinations. Each of the storage drives 315a-b may be located within the enclosure of the IHS 103A, or alternatively one or more of the storage drives 315a-b may instead be external to IHS 103A. One or more of the storage drives 315a-b may instead be located remotely from IHS 103A and may be configured as network attached storage devices. In providing storage services, IHS 103A may utilize a storage controller 314 that provides access to the two storage drives 315a-b. Storage controller 314 may be comprised of hardware and software that is configured to provide storage and retrieval of data from the storage drives 315a-b. Storage controller 314 may be configured to provide access to the storage drives 315a-b as a single logical storage device as part of a distributed data storage solution. Certain embodiments may utilize additional storage controllers that provide access to additional storage devices.

In various embodiments, an IHS 103A does not include each of the components shown in FIG. 3. In various embodiments, an IHS 103A may include various additional components in addition to those that are shown in FIG. 3. Furthermore, some components that are represented as separate components in FIG. 3 may in certain embodiments instead be integrated with other components. For example, in certain embodiments, all or a portion of the functionality provided by the illustrated components may instead be provided by components integrated into the one or more processor(s) 301 as a systems-on-a-chip.

Figure 4:
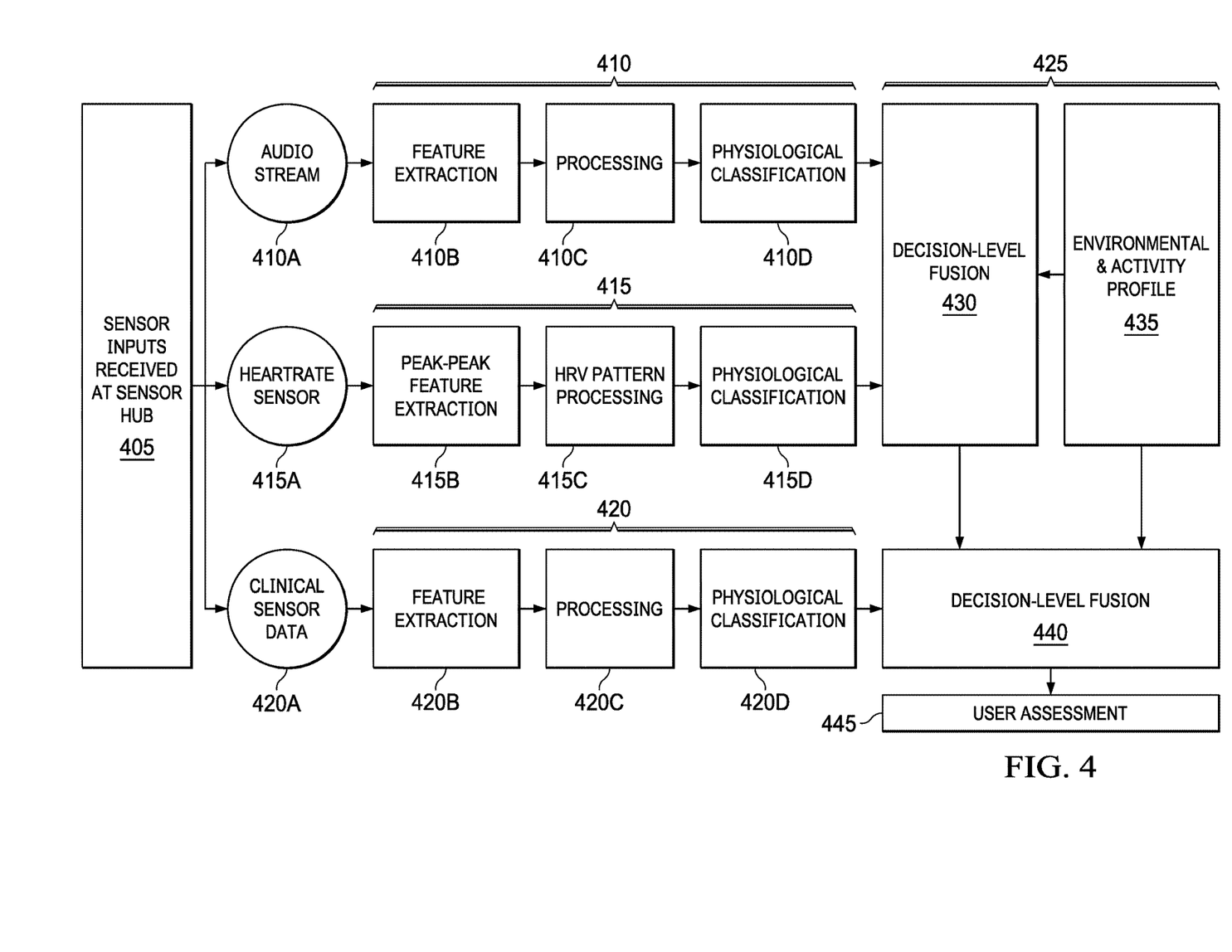
FIG. 4 is a flowchart of an example of a method for processing of physiological and environmental sensor data to generate physiological classifications for use in xR sessions, according to some embodiments.

FIG. 4 is a flowchart illustrating certain steps of a process, according to some embodiments, by which sensor data received from the various sources may be used to determine a physiological state of the user. As described with regard to FIG. 3, a host IHS may be coupled to an HMD and the host IHS may supports execution of an xR application that is presented to the user wearing the tethered HMD. The host IHS may include a sensor hub at which sensor data may be received from various devices participating in an xR session. For instance, the sensor hub of the host IHS may receive environmental sensor data from sensors that are local to the host IHS, sensors that are components of the HMD and sensors that are components of devices located within the environment of the xR session.

The sensor hub of the host IHS receives physiological data captured and streamed from sensor components of the HMD and other physiological sensors that are worn or otherwise capable of capturing physiological measurements of the user wearing the HMD. The physiological sensor data is streamed to the sensor hub of the host IHS and processed in order to determine the user's physiological attributes, such as heart rate variability patterns that may be used to determine stress levels, muscle contractions, sweat levels, and body temperature. In certain embodiments, the sensor hub of the host IHS may be configured to also receive and distribute the sensor data used to track the user's location and orientation within the xR session environment.

The illustrated embodiment begins at step 405 with the sensor hub of the host IHS receiving the physiological and environmental sensor inputs from the various sensors. As illustrated in FIG. 4, the received sensor data may be processed in multiple, independent processing chains 410, 415, 420. Using the independent processing chains, the multiple sensor data streams may be processed individually, or in combination, in order to determine, with greater certainty, the state of a user during their participation in an xR session. Each of the three processing chains in FIG. 4 is independent of the other two and arrives at local decisions regarding the user's physiological state.

As illustrated, the topmost processing chain 410 monitors streamed audio data 410a such as audio data captured by microphone components of the HMD. In certain embodiments, the sensor hub of the host IHS may utilize, at step 410b, an integrated or discrete audio DSP (Digital Signal Processing) engine of the IHS for extracting features from the audio data. The identified audio features may include periods of elevated volume and/or frequency in the voice of the user wearing the HMD. Based on processing of such features identified at step 410c, the identified audio features may be utilized at step 410d to determine a classification of the user's physiological state, such as a stress classification indicating the users level of excitement and/or stress during participation in an xR session. In certain embodiments, the physiological state classification of step 410d may include a confidence level indicating a likelihood of a correct classification.

The middle processing chain 415 monitors heartrate sensor data 415a streamed from the HMD or another device worn by the user. Similar to the processing of the audio data, features within the heartrate sensor data may be identified at step 415b. In order to identify periods of excitement or stress based on heart rate data, the feature extraction process may identify peaks within the user's heartbeat signal, as well as identifying periods of increased frequency in the user's heartbeat. In certain embodiments, these identified heartbeat features may be evaluated at step 415c against heartrate variability (HRV) patterns, where these patterns may correspond to heartrate patterns for a particular user, or for various users of a particular xR application, such as previous participants in a clinical xR session or previous players of an xR game. In certain embodiments, the patterns evaluated at step 415c may be selected based on similarity of other users to the physiological characteristics of the user. At step 415d, the heartrate variability may be used to classify the physiological state of the user, such as the user's level of excitement and/or stress. As with the audio processing chain 410, the physiological state classification of step 415d may include a confidence level indicating a likelihood of a correct classification based on the processing of the heartbeat data.

Figure 5:
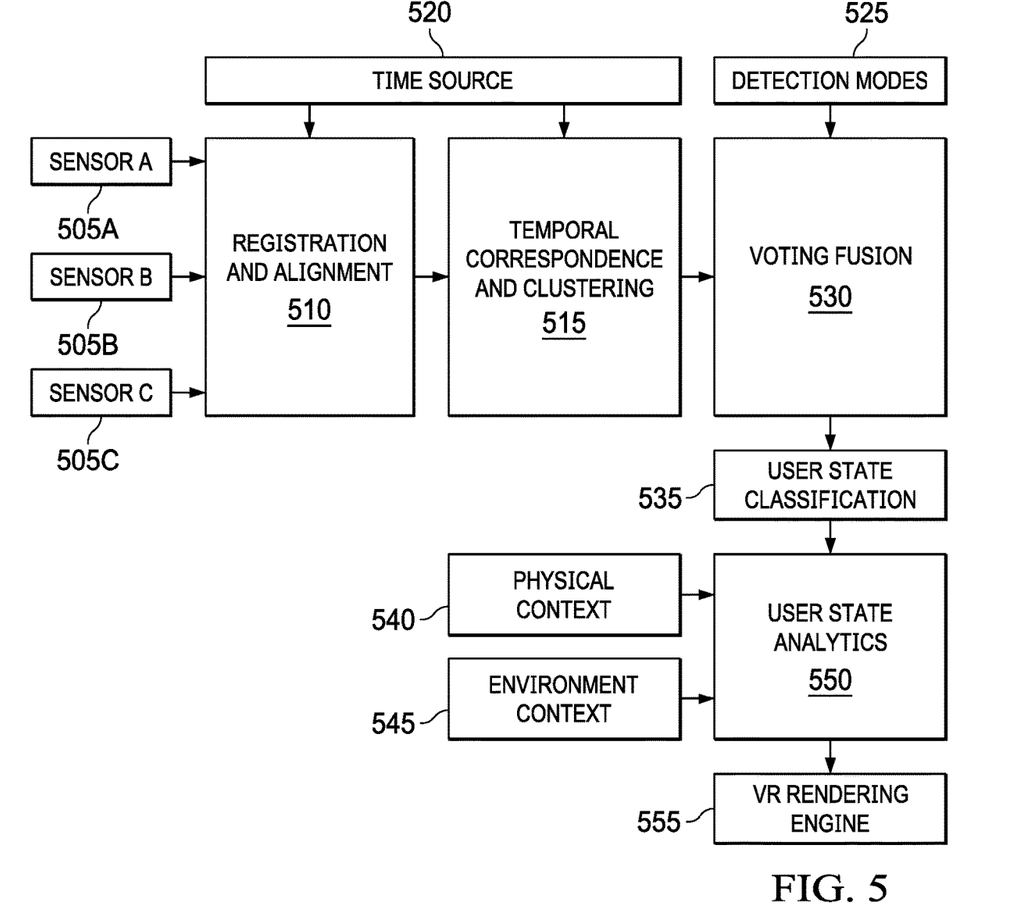
FIG. 5 is a flowchart of an example of a method, according to some embodiments, for combining the physiological and environmental data received from various sensors participating within an xR session to generate physiological classifications.
Figure 6:
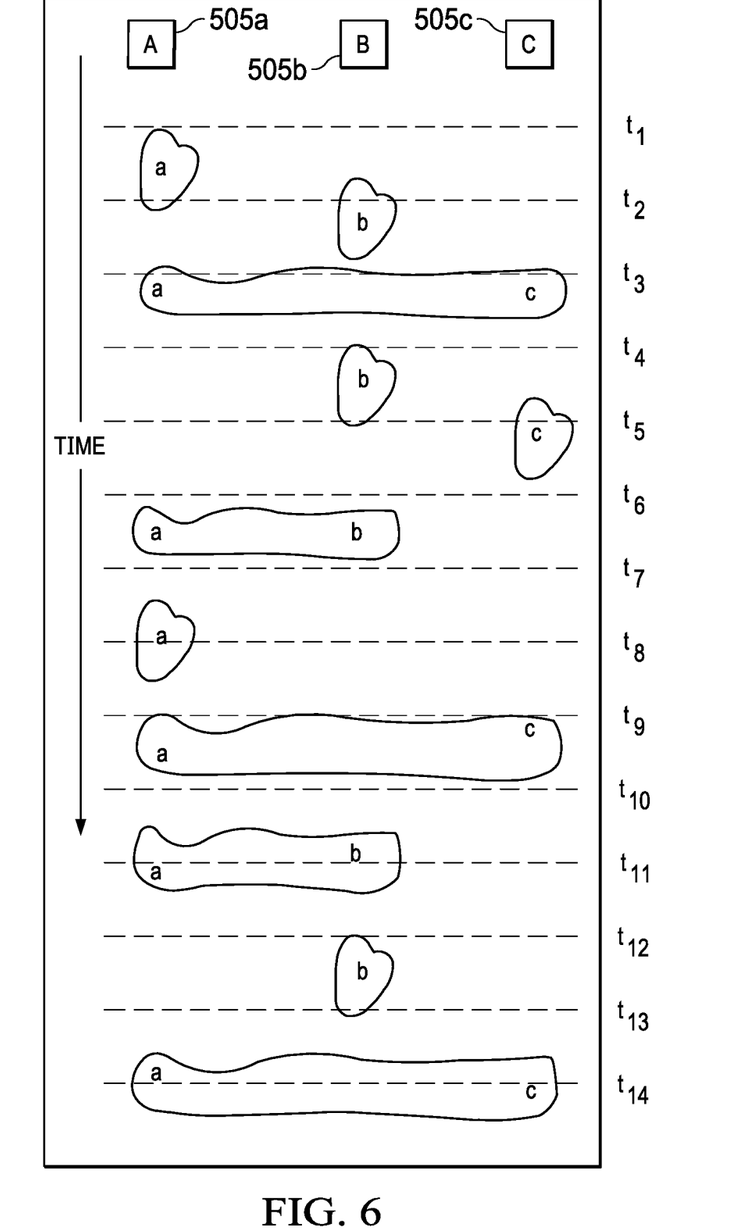
FIG. 6 is a timing diagram illustrating the asynchronous receipt and classification of sensor inputs within an xR session.

At step 430, the independent physiological classifications of the audio processing chain 410 and the heartrate processing chain 415 are combined via data fusion techniques described in additional detail with regard to FIGS. 5 and 6. Based on the combination of classifications, a higher confidence determination may be reached regarding the physiological state of the user than could be achieved based on any individual sensor stream. In certain scenarios, the data fusion techniques utilized at step 430 may be selected in order to minimize false positive determinations of excitement or stress by the user, while other scenarios may instead seek to maximize positive detections, even if at the expense of false positives, such as in a clinical setting that has been configured to minimize stress by the user.

As illustrated, the data fusion techniques utilized at step 430 may incorporate both physiological data pertaining to the user and environmental sensor data received at step 435 that characterizes the ambient environment in which an xR session is being conducted. In certain instances, the environmental conditions in which the user is participating in the xR session may affect the determination of the user's physiological state. For instance, an elevated body temperature reading may be evaluated in the context of the temperature and humidity of the xR session environment. An elevated body temperature in a colder ambient environment may indicate a higher confidence in a determination of user stress when compared to the same determination of user stress in a warmer ambient environment.

The user's current physical activity while participating in an xR session may also be received at step 435 and incorporated into the physiological state determination made at step 430. The user's participation in an xR session may include various physical activities by the user, such as participation while sitting or sedentary, walking, running, jogging or performing various types of sports and exercise motions. As with the environmental data, the activity of the user provides a context in which the physiological sensor data may be interpreted. For instance, an elevated heart rate data may be evaluated differently based on whether the user is sedentary or moving. Furthermore, an elevated heart rate be evaluated based on the intensity of the movement by the user. For instance, walking is an activity associated with a lower heart rate when compared to running. Accordingly, the confidence level of a physiological state determination made at step 430 may be modified based the environmental and physical activity context of the users xR session participation.

As illustrated, a third processing chain 420 may provide an additional independent physiological state classification for the users xR session participation. As an independent processing chain, processing chain 420 utilizes independent sensor data than the sensor data utilized by processing chains 410 or 415 such that the sensor data used by processing chain 420 is uncorrelated to the sensor data used by processing chains 410 and 415. For instance, processing chain 420 may be a processing pathway that monitors, at step 420a, sensor data other than audio data and heart rate data, such as gravimetric skin response (GSR) sensor data that provides an indication of a user's perspiration level. In certain embodiments, processing chain 420 may be implemented as part of a clinical study, such as an evaluation of GSR sensor data as indicative of stress by the user. In this manner, any number of additional, independent processing chains may be included and utilized to formulate additional determinations of the user's physiological state.

In some scenarios, processing chain 420 may be implemented by a third-party application or system that is provided access to the sensor hub data streams. In such scenarios, third-party applications may be provided in support of clinical studies that seek to utilize physiological user state information for studying, diagnosing and/or treating various types of conditions. Such clinical third parties may utilize the sensor data to provide an independent determination of the user's physiological state via processing chain 420. As with the processing of audio and heart rate data, the clinical processing chain may also utilize, at step 420b, signal-processing feature extraction techniques. The features within the sensor data may then be processed, at step 420c, and evaluated against any baseline physiological state information for the user. At step 420d, the clinical processing pathway makes its own determination regarding the physiological classification of the user based on the sensor data.

At step 440, the physiological classifications resulting from fusion of processing chains 410 and 415 and the classifications made by the clinical processing chain 420 are combined via the data fusion techniques described in additional detail with regard to FIGS. 5 and 6. As described with regard to the above processing chains, the data fusion process of step 440 may also incorporate environmental and user activity context information received at step 435 in determining the physiological state of the user. Based on this additional combination of independently-determined classifications at step 440, the confidence of the determination of the physiological state of the user may be further improved. At step 445, the physiological state determination of the user may be output to the xR application for use in adjusting the presentation of the xR session to the user.

As described with regard to FIG. 2, in HMD may include haptic components, such as micro fans and warmers, that may be operated in response to physiological state determinations made at step 445. For instance, while the user is determined to be below a threshold stress level classification, warmers may be activated in order to enhance the user's xR experience, such as to convey suspense and excitement. Similarly, cooling fans within an HMD may be utilized to enhance a peaceful xR setting that is being presented to calm the user until stress levels are detected below a specified threshold. xR applications may similarly utilize the physiological state determinations and haptic feedback inputs in a variety of manners.

For instance, in certain scenarios, game developers may tailor content based on the user's muscle activity data, heart rate, and body temperature. Clinical therapy tools for treating Post Traumatic Stress Disorder (PTSD) and phobias may adjust the presented scenarios based on the user's captured physiological data, such as heartrate, GSR moisture/sweat data, EMG muscle activity data, and as well as body temperature. Training for working within high-tension environments such as firefighting, policing, oil rigs, emergency rooms, military, and aviation, may augment or moderate xR session intensity as a function of the user's physical activity and physiological state. Educational content creators may utilize physiological inputs and feedback to enhance the teaching, discovery and learning of scientific phenomena and mathematical principles. Product designers may utilize physiological inputs and feedback to enhance the experience of users operating virtual models.

Each of the sensor processing chains 410, 415 and 420 detect physiological states of the user and reports the user state information with an associated level of confidence. The confidence values may be utilized in a manner that facilitates inference of the degree to which the physiological state determination is likely accurate. In practice, the correlation of the confidence levels with detection and false alarm probabilities may be determined from a knowledge of ground truth and actual trial detection data. For example, observed ranges of sensor values may be assigned to sensor confidence intervals that define low, medium, and high confidence regions of user state determination.

For instance, in an audio signal processing chain used to detect user excitement in a xR gaming session or stress in a clinical xR session, the detection of such conditions may be reported with a confidence value on a 10-bit scale i.e. 0-1023. A third-party clinical processing chain may detect the same conditions using a camera-based facial expression feature extraction technique, with a confidence value on an 8-bit scale of 0-255. Another clinical processing chain using HVR techniques may detect stress on a 7-bit scale of 0-127. These various confidence scales may be normalized and delineated in a manner that defines various grades of physiological states in each of the scales, thus allowing the determinations to be evaluated independently and also compared against each other.

FIG. 5 illustrates certain steps of a process according to various embodiments for multi-source data fusion using voting. In the illustrated embodiment, sensor inputs are received from three sensors: sensor A 505a, sensor B 505b and sensor C 505c. Each of these three sensors may be any of the physiological or environmental sensors described herein. The sensors inputs may be received at a sensor hub of an IHS, such as described with regard to the above embodiments. Each of the three sensors 505a-c may generate data that is reported a received asynchronously at the sensor hub. At step 510, the received asynchronous sensor inputs are aligned with regard to a time source 520 that defines discrete intervals between evaluations of user's physiological state.

Such discrete intervals are illustrated in the sequence diagram of FIG. 6. In the sequence diagram, asynchronous inputs received from three sensors 505a-c are shown in columns A-C, respectively. At t1, no sensor inputs are received. An input from sensor 505a is received between t1 and t2. An input from sensor 505b is received at t2. At t3, inputs are received from both sensors 505a and 505c. The alignment of sensor inputs to time intervals at step 510 is followed, at step 515, by clustering of the sensor inputs into sensor data groupings. For instance, clustering of sensor inputs at t11 may indicate that receipt of inputs from sensor 505a and sensor 505b. Such sensor data groupings may then be evaluated based on voting in order to determine a user's physiological state during a particular time interval.

At step 530, the sensor inputs received and available for processing during a detection interval may be combined according to data fusion techniques such as voting techniques described in detail below. The sensor data may be combined according to various detection modes received at step 525. By the selection of a detection mode, xR applications may be configured to operate in a manner that generates minimal false positive determinations of physiological user states, or in a manner that results in as many positive determinations as possible, with minimal regard for false positives. Such detection mode selections may be based on the purpose of an xR session.

For instance, a training session for high-pressure situations may purposefully seek to subject an individual to high stress, such that positive determinations of stress that will result in lessening the intensity of the xR session are not desirable unless associated with a high confidence. In such a scenario, a detection mode such as described with regard to Table 1 may be selected, in which any physiological state classification requires confirmation by two independent processing chains. Conversely, an educational session or clinical session may seek to minimize high stress situations within an xR session and may select a detection mode accordingly. In such a scenario, a detection mode such as described with regard to Table 3 may be selected, in which additional types of lower-confidence detections are sufficient to make a physiological state classification, such as a determination that the user's stress level is above a threshold. In this manner, detection mode selections received at step 525 may be used to configure the sensitivity of the detection of physiological classifications during the data fusion of step 530.

The physiological state determination resulting from the data fusion may be made at step 535. For instance, physiological state determinations may provide an indication of the level of stress or excitement by the user. As described above with regard to FIG. 4, at step 550, the physiological state determinations may be further evaluated and adjusted based on the context of the user's physical activity, received at step 540, and the characteristics of the environment in which the xR session is being conducted, received at step 545. Based on the determined physiological state of the user, at step 555, the rendering and presentation of the xR session may be modified. For instance, in certain scenarios, the intensity or difficulty of an xR session scenario may be adjusted based on the user's physiological state. Also as described, certain embodiments may support the use of haptic feedbacks for enhancing the xR session in view of the user's physiological state. For instance, in an xR environment that includes a rendering of a hot desert environment, warmers in the HMD may be activated as long as the user's excitement or stress level does not rise above a specified threshold.

In certain embodiments, other aspects of the xR session may be modified in response to a physiological state determination. As described, SLAM may be used to generate a map of landmarks within the physical environment in which an xR session is being conducted. Certain embodiments may alter the number and/or type of SLAM landmarks that are being tracked based on physiological state determinations. For instance, in scenarios where the user is determined to be in a stressed physiological state, SLAM may be adjusted to track the location of the closest and largest landmarks in order to focus available processing resources on tracking objects that could pose an immediate danger to the user. Other embodiments may alter the xR session by modifying user inputs, such as gestures, that are available as user inputs in response to a physiological state determination. For instance, in response to detecting a stressed physiological state, certain gesture inputs may be disabled, such as gestures for deleting files or other gestures for making any changes outside of the xR session. Other embodiments may alter the xR session by modifying the type of xR session that is being provided to the user. For instance, in response to a determination of a stressed physiological state, a virtual reality session may be downgraded to a mixed reality session, or to an augmented reality session. Similarly, a user may be upgraded from an augmented reality session to a mixed reality session and eventually to a virtual reality session based on detection of a specific physiological states that indicate the user's comfort with the progression.

The combination of sensor inputs in generating a classification of the user's physiological state may be achieved by voting based on the confidence levels of the user states determined using the individual sensor data streams. Referring to the embodiment of FIG. 4, each of the three processing chains 410, 415 and 420 are used to independently determine a physiological state of the user. Each of the independent processing chains generate a physiological state that may be characterized and reported with a probability of positive detection $P_d$ and a probability of false alarm $P_{fa}$. In detection modes seeking to maximize the overall probability of correctly detecting the user's physiological state, the independent user state determinations from each processing chain may be combined using a logical OR operation. Such a configuration provides the highest $P_d$, but also generates the highest number of false positive physiological state determinations.

If a detection mode seeks to minimize false positives, the generated user state classifications of the individual processing chains may be combined using a logical AND operation. Such a configuration minimizes false positives, but also suppresses the positive detection of some physiological states. For example, if the audio processing chain 410 fails to detect a particular physiological state, or does so with low confidence, and the other two chains 415, 420 correctly detect physiological state, the overall system output will still fail to declare the detection of the user's physiological state.

In order to combine the advantages of the OR and AND operations, a decision-level fusion architecture may be utilized in which the multiple, independent processing chain outputs are connected to the fusion logic, such as in FIG. 4, with each fusion block 430 and 440 utilizing different voting operations for combining the physiological state classifications generated by the different processing streams 410, 415, 420. In certain embodiments, each of the fusion blocks may utilize the algebraic voting operations specified in Tables 1-3.

TABLE 1

Four Detection Algebraic Voting Modes

| | Source and Confidence Level | | |
|---|---|---|---|
| Mode | A (Audio) | B (Heart Rate) | C ($3^{rd}$ Party) |
| ABC | $A_1$ | $B_1$ | $C_1$ |
| AC | $A_2$ | — | $C_2$ |
| BC | — | $B_2$ | $C_2$ |
| AB | $A_3$ | $B_3$ | — |

System Output=$(A_1 \& B_1 \& C_1)|(A_2 \& C_2)|(B_2 \& C_2)|(A_3 \& B_3)$

Table 1 illustrates a data fusion solution that uses four source voting modes for categorizing sensor inputs as indicative of a particular physiological state. In this case, none of the sources can individually generate a physiological state classification. Instead, collaborating votes from multiple sources are required in order to make a physiological state classification. In such a conservative system, few false alarms are likely to be generated. However, the probability of detection may also suffer since even high confidence sources ($A_3$ and $B_3$) cannot individually vote the presence of targets.

TABLE 2

Six Detection Algebraic Voting Modes

| | Source and Confidence Level | | |
|---|---|---|---|
| Mode | A (Audio) | B (Heart Rate) | C ($3^{rd}$ Party) |
| ABC | $A_1$ | $B_1$ | $C_1$ |
| AB | $A_2$ | $B_2$ | — |
| AC | $A_2$ | — | $C_2$ |
| BC | — | $B_2$ | $C_2$ |
| A | $A_3$ | — | — |
| B | — | $B_3$ | — |

System Output=$(A_1 \& B_1 \& C_1)|(A_2 \& B_2)|(A_2 \& C_2)|(B_2 \& C_2)|A_3|B_3$ The Table 2 illustrates a six-vote mode that provides a three-source data fusion solution. The voting solution of Table 2 includes two single-vote classifications that may be made based on particular high-confidence sensor readings ($A_3$ and $B_3$). Such single vote classifications may increase positive detections. In order to limit false positives, all detections based on medium-confidence sensor readings ($A_2$, $B_2$, and $C_2$) require a vote of a supporting physiological state detection generated by other medium confidence sensor readings determinations.

TABLE 3

Eleven Detection Algebraic Voting Modes

| | Source and Confidence Level | | |
|---|---|---|---|
| Mode | A (Audio) | B (Heart Rate) | C ($3^{rd}$ Party) |
| AB | $A_1$ | $B_1$ | — |
| | $A_2$ | $B_1$ | — |
| | $A_2$ | $B_2$ | — |
| | $A_1$ | $B_2$ | — |

TABLE 3-continued

Eleven Detection Algebraic Voting Modes

| Mode | A (Audio) | B (Heart Rate) | C (3$^{rd}$ Party) |
|---|---|---|---|
| AC | $A_1$ | — | $C_1$ |
|  | $A_2$ | — | $C_1$ |
| BC | — | $B_1$ | $C_1$ |
|  | — | $B_2$ | $C_1$ |
| A | $A_3$ | — | — |
| B | — | $B_3$ | — |
| C | — | — | $C_3$ |

System Output=$(A_1 \& B_1)|(A_2 \& B_1)|(A_2 \& B_2)|(A_1 \& B_2)|(A_1 \& C_1)|(A_2 \& C_1)|(B_1 \& C_1)|(B_2 \& C_1)|A_3|B_3|C_3$ Table 3 illustrates the use of an expanded detection space. In this table, the three-vote classification based on the combination of medium confidence sensor readings ($A_2$, $B_2$, and $C_2$) is no longer included, thus improving the probability of detection of a physiological state. Instead, all two-vote mode combinations at low and medium confidence are utilized. In addition, all sources may generate a physiological state classification based on a single-vote, high confidence sensor inputs ($A_3$, $B_3$, and $C_3$).

It should be understood that various operations described herein may be implemented in software executed by logic or processing circuitry, hardware, or a combination thereof. The order in which each operation of a given method is performed may be changed, and various operations may be added, reordered, combined, omitted, modified, etc. It is intended that the invention(s) described herein embrace all such modifications and changes and, accordingly, the above description should be regarded in an illustrative rather than a restrictive sense.

Although the invention(s) is/are described herein with reference to specific embodiments, various modifications and changes can be made without departing from the scope of the present invention(s), as set forth in the claims below. Accordingly, the specification and figures are to be regarded in an illustrative rather than a restrictive sense, and all such modifications are intended to be included within the scope of the present invention(s). Any benefits, advantages, or solutions to problems that are described herein with regard to specific embodiments are not intended to be construed as a critical, required, or essential feature or element of any or all the claims.

Unless stated otherwise, terms such as "first" and "second" are used to arbitrarily distinguish between the elements such terms describe. Thus, these terms are not necessarily intended to indicate temporal or other prioritization of such elements. The terms "coupled" or "operably coupled" are defined as connected, although not necessarily directly, and not necessarily mechanically. The terms "a" and "an" are defined as one or more unless stated otherwise. The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, device, or apparatus that "comprises," "has," "includes" or "contains" one or more elements possesses those one or more elements but is not limited to possessing only those one or more elements. Similarly, a method or process that "comprises," "has," "includes" or "contains" one or more operations possesses those one or more operations but is not limited to possessing only those one or more operations.

The invention claimed is:

1. A method for hosting a virtual, augmented, or mixed reality (xR) session in a first physical environment, comprising:
    receiving a plurality of physiological data streams during a first time interval, each of the data streams comprising physiological measurements of an individual wearing a Head-Mounted Device (HMD) while participating in the xR session during the first time interval;
    determining a first physiological user state during the first time interval based on a first of the data streams by a first processing chain wherein the first processing chain determines the first physiological user state with a first confidence level;
    determining a second physiological user state during the first time interval based on a second of the data streams by a second processing chain, wherein the second processing chain determines the second physiological state with a second confidence level;
    combining the first physiological state and the second physiological state to determine a cumulative physiological user classification during the time interval, wherein the first and second physiological states are combined by each providing a vote on the cumulative physiological user classification, and wherein the votes by each of the first and second physiological states are combined using conjunctive and disjunctive operations that use the votes as inputs; and
    modifying the xR session based on the cumulative physiological user classification.

2. The method of claim 1, wherein the conjunctive and disjunctive operations that are selected for use in combining the votes of the first and second physiological states are selected based on the respective confidence levels of the physiological user states.

3. The method of claim 1, wherein the first and second physiological states are combined using disjunctive operations when the confidence levels of the respective user states are above a threshold indicating a high degree of confidence in the user state determinations.

4. The method of claim 1, wherein the cumulative physiological user classification determined based on the voting operations of the first and second physiological states indicates a physiological stress level of the individual while participating in the xR session.

5. The method of claim 4, wherein the xR session is modified by converting the xR session from a virtual reality session to an augmented reality session or a mixed reality session in response to the physiological stress level of the individual exceeding a threshold.

6. The method of claim 1, wherein the conjunctive and disjunctive operations that are selected for use in combining the votes of the first and second physiological states are selected in order to reduce false positive determinations of the cumulative physiological user classification.

7. The method of claim 1, wherein the conjunctive and disjunctive operations that are selected for use in combining the first physiological user state and the second physiological user state are selected in order to increase positive determinations of the cumulative physiological user classification.

8. A Head-Mounted Device (HMD) configured for participating in a virtual, augmented, or mixed reality (xR) session in a first physical environment, comprising:

a processor;
a plurality of physiological sensors, each physiological sensor generating a data stream including physiological measurements of an individual wearing the HMD while participating in the xR session; and
a memory coupled to the processor, the memory having program instructions stored thereon that, upon execution, cause the first HMD to:
  transmit the plurality of physiological data streams to a host IHS (Information Handling System), wherein a first physiological user state is determined based on a first of the data streams by a first processing chain of the host IHS, and wherein a second physiological user state is determined based on a second of the data streams by a second processing chain of the IHS;
  wherein the first and second physiological states are combined by the host IHS to determine a cumulative physiological user classification, wherein the first and second physiological states are combined by each providing a vote on the cumulative physiological user classification, and wherein the votes by each of the first and second physiological states are combined using conjunctive and disjunctive operations that use the votes as inputs, and wherein the xR session is modified based on the cumulative physiological user classification; and
  presenting the modified xR session to the individual.

9. The HMD of claim 8, wherein the modifications to the xR session based on the cumulative physiological user classification comprises modifying landmarks that are tracked in the first physical environment.

10. The HMD of claim 9, wherein, when the cumulative physiological user classification indicates a physiological stress level of the individual above a threshold while participating in the xR session, the modification of the landmark tracking comprises tracking a selection of the landmarks that are in closest proximity to the individual.

11. The HMD of claim 9,
  wherein, when the cumulative physiological user classification indicates a physiological stress level of the individual above a threshold while participating in the xR session, the modification of the landmark tracking comprises tracking a selection of the largest landmarks in the first physical environment.

12. The HMD of claim 8, wherein the first and second physiological states are combined using conjunctive operations when the confidence levels of the respective user states are below a threshold indicating a low degree of confidence in the user state determinations.

13. The HMD of claim 8, wherein the xR session is modified by reducing the user inputs that are available to the user in the xR session in response to the cumulative physiological user classification of the individual indicating a stressed physiological classification.

14. The HMD of claim 8, wherein the xR session is modified by converting the xR session from an augmented reality session to a mixed reality session or a virtual reality session in response to the cumulative physiological user classification indicating a stress level below a threshold.

15. A system for hosting a virtual, augmented, or mixed reality (xR) session in a first physical environment, comprising:
a Head-Mounted Device (HMD) comprising a plurality of physiological sensors, each physiological sensor generating a data stream including physiological measurements of an individual wearing the HMD while participating in the xR session; and
a host IHS (Information Handling System) coupled to the HMD and configured to:
  receive the plurality of physiological data streams;
  determine a first physiological user state based on a first of the data streams by a first processing chain, and wherein the first processing chain determines the first physiological user state with a first confidence level;
  determine a second physiological user state based on a second of the data streams by a second processing chain, wherein the second processing chain determines the second physiological state with a second confidence level;
  combine the first physiological state and the second physiological state to determine a cumulative physiological user classification, wherein the first and second physiological states are combined by each providing a vote on the cumulative physiological user classification, and wherein the votes by each of the first and second physiological states are combined using conjunctive and disjunctive operations that use the votes as inputs, wherein the conjunctive and disjunctive operations are selected based on the respective confidence levels of the first and second physiological states; and
  modify the presentation of the xR session to the individual by the HMD based on the cumulative physiological user classification.

16. The system of claim 15, wherein the first and second physiological states are combined using disjunctive operations when the confidence levels of the respective user states are above a threshold indicating a high degree of confidence in the user state determinations.

17. The system of claim 15, wherein the cumulative physiological user classification determined based on the voting operations of the first and second physiological states indicates a physiological stress level of the individual while participating in the xR session.

18. The system of claim 17, wherein the xR session is modified by decreasing an intensity level of the xR session in response to the physiological stress level of the individual above a threshold.

19. The system of claim 15, wherein the first and second physiological states are combined using conjunctive and disjunctive operations that use the votes as inputs by a sensor hub of the of the host IHS.

20. The system of claim 15, wherein the conjunctive and disjunctive operations that are selected for use in combining the first physiological user state and the second physiological user state are selected in order to increase positive determinations of the cumulative physiological user classification.

* * * * *